(12) United States Patent
Weeden

(10) Patent No.: US 9,416,905 B2
(45) Date of Patent: Aug. 16, 2016

(54) PROTECTIVE COVER FOR DRAINAGE TUBE CABLE TIE

(71) Applicant: Jeffrey A. Weeden, Bolingbrook, IL (US)

(72) Inventor: Jeffrey A. Weeden, Bolingbrook, IL (US)

( * ) Notice: Subject to any disclaimer, the term of this patent is extended or adjusted under 35 U.S.C. 154(b) by 0 days.

(21) Appl. No.: 14/940,853

(22) Filed: Nov. 13, 2015

(65) Prior Publication Data

US 2016/0208975 A1    Jul. 21, 2016

Related U.S. Application Data

(60) Provisional application No. 62/106,026, filed on Jan. 21, 2015.

(51) Int. Cl.
  *A61M 25/02*    (2006.01)
  *F16L 55/07*    (2006.01)

(52) U.S. Cl.
  CPC ............... *F16L 55/07* (2013.01); *A61M 25/02* (2013.01); *A61M 2025/026* (2013.01)

(58) Field of Classification Search
  CPC .............. A61M 25/02; A61M 2025/0253; A61M 2025/026; F16L 33/02; F16L 55/07
  USPC ............ 604/43, 326; 285/45, 23, 148.3, 200, 285/260; 606/157, 158, 151; 24/16 PB, 24/17 AP, 483
  See application file for complete search history.

(56) References Cited

U.S. PATENT DOCUMENTS

| 4,018,221 A | * | 4/1977 | Rennie | A61M 16/0683 128/207.18 |
| 4,088,136 A | * | 5/1978 | Hasslinger | A61M 25/02 604/179 |
| 4,221,215 A | * | 9/1980 | Mandelbaum | A61F 13/02 604/326 |

(Continued)

*Primary Examiner* — David E Bochna
(74) *Attorney, Agent, or Firm* — Christopher C. Dremann, P.C.; Christopher C. Dremann

(57) ABSTRACT

A protective cover for a drainage tube cable tie protects a surgical patient from injury and/or infection. The protective cover includes a first fastener member having VELCRO® hooks on one side and pressure sensitive adhesive on the other side, a second fastener member having VELCRO® loops on one side and pressure sensitive adhesive on the other side, and an insert made of a flexible, relatively elastic material. An opening is formed through the first fastener member. The insert is placed over the opening and the pressure sensitive adhesive sides of the fastener members are pressed together in back-to-back relationship. The cable tie is positioned on the first fastener member over the opening and the insert, and the protective cover is wrapped around the cable tie and secured by engagement of the hooks with the loops to cover the cable tie and protect the patient's skin.

20 Claims, 6 Drawing Sheets

(56) References Cited

U.S. PATENT DOCUMENTS

| | | | | |
|---|---|---|---|---|
| 4,379,009 A * | 4/1983 | Shibata | F16L 23/00 285/45 |
| 4,569,348 A * | 2/1986 | Hasslinger | A61M 25/02 604/179 |
| 4,571,245 A * | 2/1986 | Hubbard | A61M 25/02 604/179 |
| 4,617,017 A * | 10/1986 | Hubbard | A61M 25/02 604/179 |
| 4,639,980 A * | 2/1987 | Peterson | A61M 25/02 24/302 |
| 4,700,432 A * | 10/1987 | Fennell | B65D 63/16 24/16 PB |
| 4,738,661 A * | 4/1988 | Marut | A61F 13/148 604/345 |
| 4,821,736 A * | 4/1989 | Watson | A61B 5/0836 128/207.17 |
| 4,930,543 A * | 6/1990 | Zuiches | F16L 35/00 285/45 |
| 4,979,613 A * | 12/1990 | McLaughlin | B65D 33/24 24/304 |
| 5,048,512 A * | 9/1991 | Turner | A61J 15/0015 128/876 |
| 5,086,543 A * | 2/1992 | Mitchell | A44B 18/00 24/16 PB |
| 5,163,914 A * | 11/1992 | Abel | A61M 25/02 128/200.24 |
| 5,168,603 A * | 12/1992 | Reed | A44B 18/00 24/16 PB |
| 5,214,874 A * | 6/1993 | Faulkner | A01K 87/00 128/DIG. 15 |
| 5,352,209 A * | 10/1994 | Bird | A61M 25/02 128/DIG. 26 |
| 5,517,838 A * | 5/1996 | Moore | E05B 13/002 24/16 PB |
| 5,527,070 A * | 6/1996 | Blackwell | F16L 57/00 138/105 |
| 5,549,567 A * | 8/1996 | Wolman | A61M 25/02 128/DIG. 26 |
| 5,616,205 A * | 4/1997 | Cogdill | F16L 33/02 156/229 |
| 5,879,335 A * | 3/1999 | Martinez | A61M 25/02 604/179 |
| 5,897,519 A * | 4/1999 | Shesol | A61M 25/02 602/75 |
| 5,918,599 A * | 7/1999 | Shesol | A61M 16/0465 128/207.17 |
| 6,258,066 B1 * | 7/2001 | Urich | A61M 25/02 604/174 |
| 6,436,074 B1 * | 8/2002 | Lee | A61M 25/02 604/174 |
| 7,185,399 B2 * | 3/2007 | Logan | F16L 3/233 24/16 PB |
| 7,284,729 B2 * | 10/2007 | Walsh | A61M 25/02 24/16 R |
| 7,284,730 B2 * | 10/2007 | Walsh | A61M 25/02 128/877 |
| 8,479,361 B2 * | 7/2013 | Every | B65D 63/1063 24/16 PB |
| 8,726,468 B2 * | 5/2014 | Dyer | B65D 63/1063 24/16 PB |

* cited by examiner

PROTECTIVE COVER FOR DRAINAGE TUBE CABLE TIE

FIELD OF THE INVENTION

The present invention relates generally to devices and methods for protecting a surgical patient from injury and/or infection. More particularly, the invention is a protective cover and associated method for protecting a surgical patient from the sharp or jagged edge of a cable tie used to connect surgical drainage tubes.

BACKGROUND OF THE INVENTION

Most surgery patients, and especially lung, heart and stomach surgery patients, require one or more drainage tubes for draining bodily fluids during post-operative recovery. A relatively small diameter tube is inserted into the patient's lung, chest cavity and/or stomach during surgery. The smaller diameter tube is then connected to a larger diameter drainage tube outside the patient's body for delivering the body fluids to a collection container. The larger diameter drainage tube is typically connected to the smaller diameter drainage tube by an adjustable diameter connecting tie, commonly referred to as a cable tie. The smaller diameter drainage tube is inserted into the larger diameter drainage tube to create an overlapping area of the drainage tubes. The cable tie is positioned around the overlapping area of the drainage tubes, and a free end of the cable tie is passed through a one-way slotted head provided on the opposite end of the cable tie. The free end is pulled through the slotted head until the cable tie is taut around the overlapping area on the outer periphery of the larger diameter drainage tube. In this manner, the drainage tubes are connected together and secured from being pulled apart by normal movements of the patient or the drainage tubes.

The excess length of the free end of the cable tie beyond the slotted head is typically cut away so that it does not become entangled with or snagged on the clothing of health care personnel treating the patient, the patient's clothing (e.g., hospital gown) and/or the patient's bedding. Unfortunately, it is nearly impossible to cut the free end of the cable tie close to the slotted head without leaving a sharp or jagged edge. The sharp or jagged edge on the cable tie can contact and rub against the patient's skin when the patient moves or when the drainage tubes are moved relative to the patient. At the very least, contact with the sharp or jagged edge of the cable tie is a source of discomfort for the patient. More seriously, however, repeated contact with the sharp or jagged edge of the cable tie causes irritation and/or injury, such as cuts and scrapes, to the skin of the patient. In some instances, the area of the irritation and/or injury to the patient's skin may become a source of infection. It is well documented that hospital acquired staph infections, also known as nosocomial infections, such as Methicillin-Resistant *Staphylococcus Aureus* (MRSA), are a leading cause of post-surgical complications, including death, among post-operative surgical in-patients.

It is known for nurses and other health care personnel to wrap surgical tape around a cable tie connecting drainage tubes to prevent the sharp or jagged edge of the free end of the cable tie from coming into contact with the patient's skin. However, dressing each cable tie with surgical tape can be tedious and time consuming, especially when a post-operative surgical patient has a number of drainage tubes, which in the case of a heart or lung surgery can be as many as nine different drainage tubes having at least two interconnections each. In addition, surgical tape can easily separate from itself and/or the cable tie if not applied properly and expose the adhesive of the tape to the ambient environment and to the patient's skin—thereby further increasing the risk of infection.

It is therefore apparent that a need exists for a device and method for protecting a surgical patient from injury and/or infection. A more particular need exists for a device and associated method for protecting a surgical patient from the sharp or jagged edge of a cable tie used to interconnect surgical drainage tubes. A specific need exists for such a device and method that relieves discomfort to the patient and reduces the incidence of nosocomial infections. In addition, the device and method needs to be relatively simple and fast for health care personnel to apply with little or no risk that the device will separate from itself or the cable tie and expose the patient to an adhesive.

Certain aspects, objects, features and advantages of the present invention will be made apparent, or will be readily understood and appreciated by those skilled in the relevant art, as exemplary embodiments of the invention shown in the accompanying drawing figures are described in greater detail hereinafter. It is intended that all such aspects, objects, features and advantages of the invention envisioned by this disclosure of exemplary embodiments are encompassed by the scope of the appended claims, given their broadest reasonable construction and interpretation. These aspects, objects, features and advantages of the invention, as well as others not expressly disclosed, may be accomplished by any of the exemplary embodiments described herein and illustrated in the accompanying drawings. However, it should be appreciated that the drawing figures are for illustrative purposes only, and that many modifications, changes, revisions and substitutions may be made to any of the exemplary embodiments without departing from the intended broad construction and interpretation of the general concepts of the invention.

BRIEF DESCRIPTION OF THE DRAWINGS

The aforementioned aspects, objects, features and advantages of the present invention will be more fully understood and appreciated when considered in conjunction with the accompanying drawing figures, in which like reference characters designate the same or similar parts throughout the several views.

DETAILED DESCRIPTION OF EXEMPLARY EMBODIMENTS OF THE INVENTION

Figure 1:
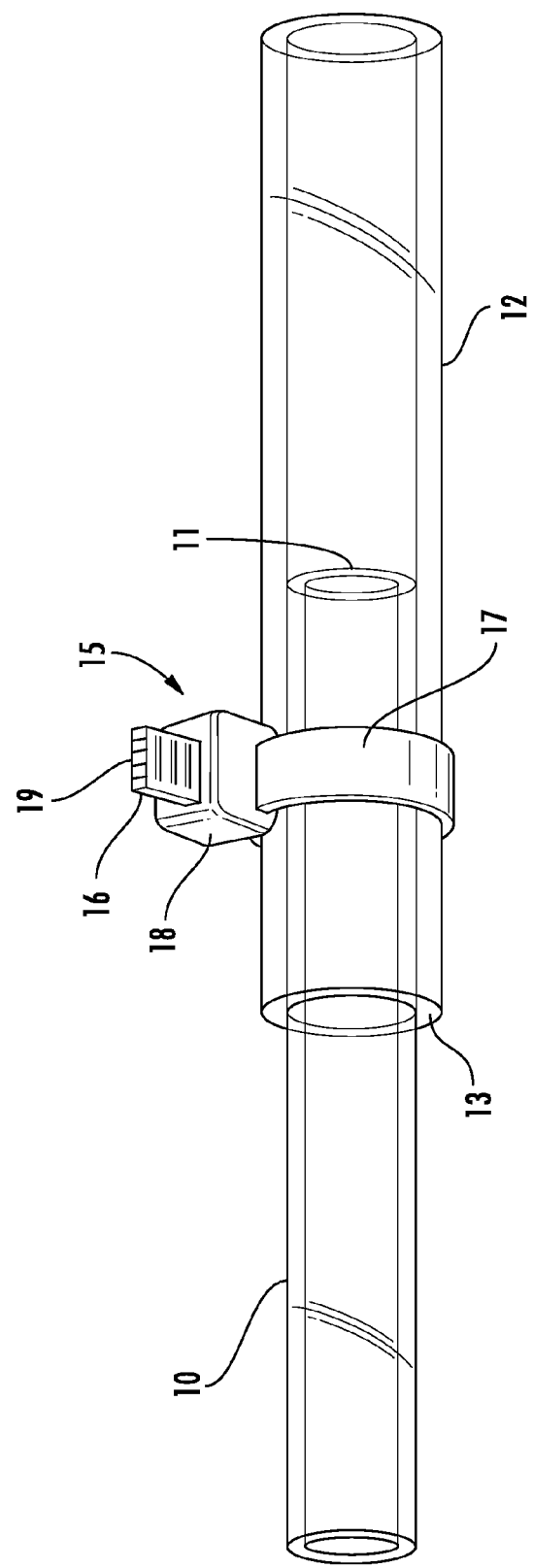
FIG. 1 is a perspective view showing a cable tie interconnecting a smaller diameter drainage tube with a larger diameter drainage tube.

As previously discussed, one or more drainage tubes, commonly referred to as a surgical drain, are typically used to drain fluids (e.g., pus, blood, bodily fluids) from a wound as the wound heals. In the case of an evasive internal surgery, such as heart or lung surgery, a patient may have as many as nine different drainage tubes inserted into the lung, chest or stomach cavity. A smaller diameter drainage tube generally exits the patient's body and is interconnected with a larger diameter drainage tube leading to a collection bottle, bag, bulb or the like for collecting the fluids. The smaller diameter drainage tube is typically interconnected with the larger diameter drainage tube by a conventional fastener, commonly referred to as a cable tie. A cable tie, also known as a tie-wrap, hose tie, zap-strap or zip tie, is normally made of nylon and has a tape section with teeth that engage a pawl in a slotted head provided at one end of the tape section to form a ratchet. Thus, the opening defined by the cable tie decreases as the free end of the tape section is fed through the slotted head and the cable tie tightens around the larger diameter drainage tube to secure the larger diameter drainage tube onto the smaller diameter drainage tube. The excess length of the free end of the tape section is then cut or severed and removed adjacent the slotted head. Unfortunately, a sharp or jagged edge of the free end of the cable tie remains at the location of the connection between the smaller diameter drainage tube and the larger diameter drainage tube.

Given the improvements and increased confidence in surgical techniques, there is a growing controversy within the medical community whether the benefits of surgical drains outweigh the associated risks. In particular, drains have a tendency to become occluded or clogged, resulting in fluids being retained that can contribute to infection. In addition, the sharp or jagged edge of the free end of the cable tie is a further catalyst for infection. The sharp or jagged edge on the cable tie can cut, scratch, scrape or irritate the patient's skin when the drainage tube or the patient moves. The resulting cut, scratch, scrape or irritation can subsequently become infected due to bacteria present on the drainage tubes, the patient's clothing, the patient's bedding, health care personnel and/or the surrounding area. It is well established that hospital acquired staph infections, or nosocomial infections, such as Methicillin-Resistant *Staphylococcus Aureus* (MRSA), are a leading cause of post-surgical complications, including death, among post-operative surgical in-patients. The present invention relates to a protective cover, indicated generally herein by reference character 20, that can be quickly and easily applied by health care personnel to protect a surgical patient from the sharp or jagged edge of a cable tie used to connect surgical drainage tubes. The protective cover eliminates discomfort to the patient from contact with the sharp or jagged edge of the cable tie and reduces the likelihood of infection to a cut, scratch, scrape or irritation of the patient's skin resulting from contact with the sharp or jagged edge of the cable tie.

FIG. 1 shows a smaller diameter drainage tube, indicated generally by reference character 10, interconnected with a larger diameter drainage tube, indicated generally by reference character 12, by a conventional cable tie, indicated generally by reference character 15, as previously described. The drainage tubes 10, 12 may be any substantially hollow tube suitable for use with a patient and made of a medical grade material, such as a biologically inert plastic. By way of example and not limitation, the drainage tubes 10, 12 may be made of a thin-walled, relatively small bore fluorosilicone elastomer, such as SILASTIC® high consistency silicone rubber (HCSR) commercially available from Dow Corning Corporation of Midland, Mich., USA. A first end (not shown) of the smaller diameter drainage tube 10 extends from a body cavity of a patient, for example a post-operative surgical patient. The opposite, or second, end 11 of the smaller diameter drainage tube 10 is inserted into a first end 13 of the larger diameter drainage tube 12. The opposite, or second, end (not shown) of the larger diameter drainage tube 12 is routed to a collection bag, bottle, bulb or the like for collecting fluids (e.g., pus, blood bodily fluids) from the body cavity of the surgical patient. The smaller diameter drainage tube 10 and the larger diameter drainage tube 12 are connected together by the cable tie 15 in a well known and conventional manner.

Of relevance to the present invention, the free end 16 of the tape section 17 of the cable tie 15 is fed through the slotted head 18 of the cable tie until an opening defined by the cable around the larger diameter drainage tube 12 decreases sufficiently to engage the first end 13 of the larger diameter drainage tube onto the second end 11 of the smaller diameter drainage tube 10 so that the smaller diameter drainage tube 10 is secured within the larger diameter drainage tube 12. As previously mentioned, the excess length of the free end 16 of the tape section 17 of cable tie 15 is cut or severed adjacent to the slotted head 18. As a result, the free end 16 of the cable tie 15 creates a sharp or jagged edge 19 adjacent the slotted head 18 at the location of the connection between the smaller diameter drainage tube 10 and the larger diameter drainage tube 12. The cable tie 15 can be a source of discomfort to the post-operative surgical patient if movement of the patient or the drainage tubes 10, 12 causes the sharp or jagged edge 19 of the cable tie to contact the skin of the patient. In particular, any cut, scratch, scrape or irritation to the skin of the patient caused by contact with the sharp or jagged edge 19 of the cable tie 15 increases the risk of the patient developing a nosocomial infection, such as MRSA.

Figure 2:
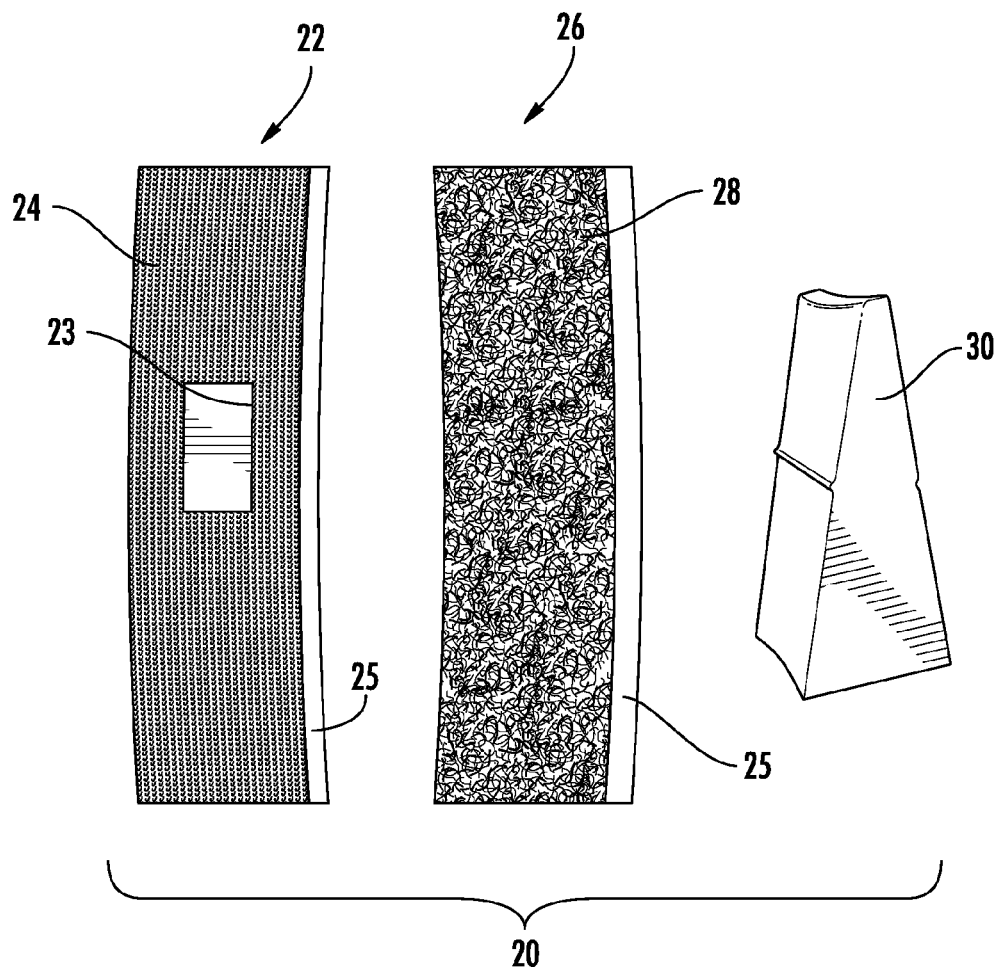
FIG. 2 is a plan view showing the components of an exemplary embodiment of a protective cover according to the present invention for protecting a surgical patient from injury and/or infection shown in an unassembled configuration.
Figure 3:
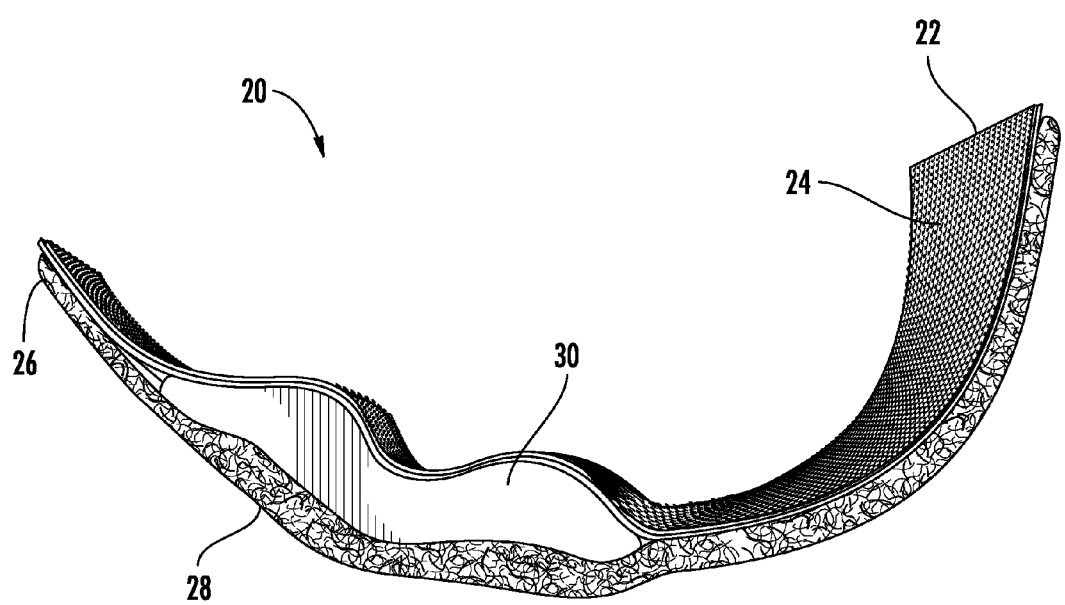
FIG. 3 is a perspective view of a protective cover according to the present invention for protecting a surgical patient from injury and/or infection shown in an assembled configuration.

FIG. 2 shows the components of an exemplary embodiment of a protective cover 20 according to the present invention in an unassembled configuration. FIG. 3 shows the components of the protective cover 20 in an assembled configuration. The protective cover 20 comprises a first fastener member 22, a second fastener member 26 and a flexible, relatively elastic insert 30 configured to be disposed between the first fastener member 22 and the second fastener member 26, as will be described. The first fastener member 22 is a relatively short length of a low-profile fastener tape. A suitable low-profile fastener tape is commercially available from Levitt Industrial Textile of Westbury, N.Y., USA, and is sold under the trademark ULTRA-MATE®. The ULTRA-MATE® fastener tape has a pressure sensitive adhesive backing on one side (not shown) and a pattern of VELCRO® type hooks 24 on the opposite, other side. The second fastener member 26 is likewise a relatively short length of a low-profile fastener tape. A suitable low-profile fastener tape is the ULTRA-MATE® fastener tape available from Levitt Industrial Textile having a pressure sensitive adhesive backing on one side (not shown) and a pattern of VELCRO® type loops 28 on the opposite, other side. Each of the first fastener member 22 and the second fastener member 26 may have a relatively thin releasable film 25 covering the pressure sensitive adhesive backing prior to assembly. The VELCRO® type hooks 24 of the first fastener member 22 and the VELCRO® type loops 28 of the second fastener member 26 cooperate with one another to provide a conventional VELCRO® style fastener in a well known manner.

The first fastener member 22 and the second fastener member 26 may have any desired length and width suitable for covering the cable tie 15 at the location of the connection between the drainage tubes 10, 12. In one advantageous embodiment, the first and second fastener members 22, 26 may each have a length of about five (5) inches and a width of about one (1) inch. However, other reasonable lengths and widths are possible without departing from the purpose and intent of the invention. Regardless, an opening 23 is formed through the thickness of the first fastener member 22 having dimensions that are configured (i.e., sized and shaped) to receive at least the slotted head 18 and the edge 19 on the free end 16 of the tape section 17 of the cable tie 15. As illustrated by the exemplary embodiment herein, the opening 23 is generally rectangular and is between about one-quarter (¼) inches and about three-quarters (¾) inches in width, and between about one (1) inch and about one and one-half (1½) inches in length.

The insert 30 may be made of any suitable material having sufficient flexibility and resilience to receive the slotted head 18 and the edge 19 on the free end 16 of the tape section 17 of the cable tie 15. One example of a suitable material for insert 30 is high density urethane foam of the type commercially available from Uline Corporation of Pleasant Prairie, Wis., USA. The insert 30 may have any suitable configuration (i.e., size and shape) that is compatible with the dimensions of the first and second 22, 26 fastener members. In one advantageous embodiment, the insert 30 may be about two (2) inches in length, about one (1) inch in width, and between about one-half (½) inch and about one (1) inch thick. Furthermore, the thickness of the insert 30 may be sculpted as desired. For example, the thickness of the insert 30 may be about one-half (½) inch at one lengthwise end and about one (1) inch at the other lengthwise end of the insert.

Figure 4:
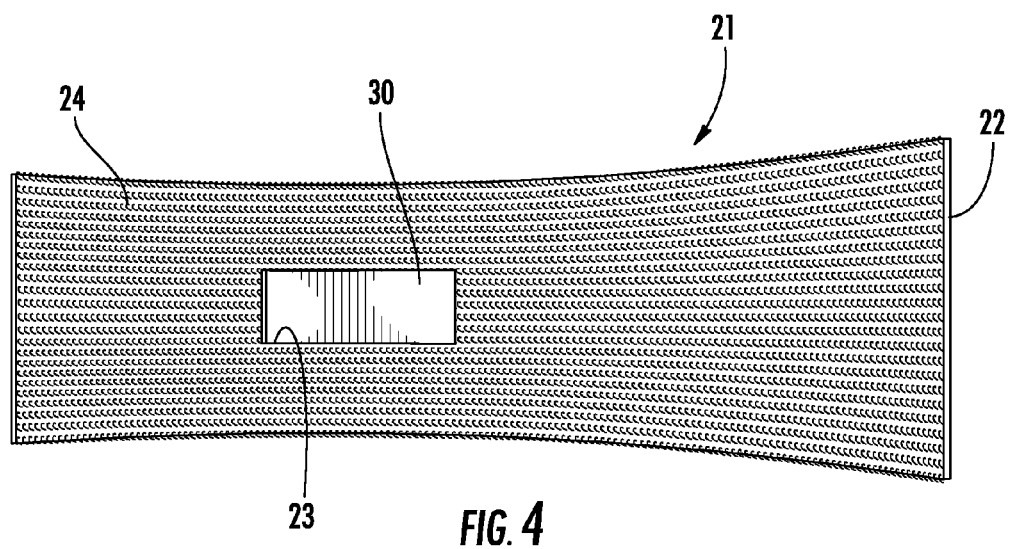
FIG. 4 is a plan view showing a first side of the protective cover.

The releasable film 25 is removed from the other side of the first fastener member 22 and the insert 30 is positioned over the opening 23 and onto the pressure sensitive adhesive. The releasable film 25 is then removed from the other side of the second fastener member 26 and the pressure sensitive adhesive backings of the first and second fastener members 22, 26 are pressed together in back-to-back relationship to adhere the fastener members together with the VELCO® hooks 24 facing outwardly on one side and the VELCRO® loops 28 facing outwardly on the opposite side of the assembly. FIG. 4 shows a first side 21 of the assembled protective cover 20 having the first fastener member 22 with the VELCRO® hooks 24 and the opening 23 exposing a portion of the insert 30 disposed between the first fastener member 22 and the second fastener member 26. Insert 30 is exposed through the opening 23 of the first fastener member 22 to cover the slotted head 18 and the edge 19 of the cable tie 15, as will be next described. An opposite second side 29 (FIG. 6) of the assembled protective cover 20 has the second fastener member 26 with the VELCRO® loops 28 thereon.

Figure 5:
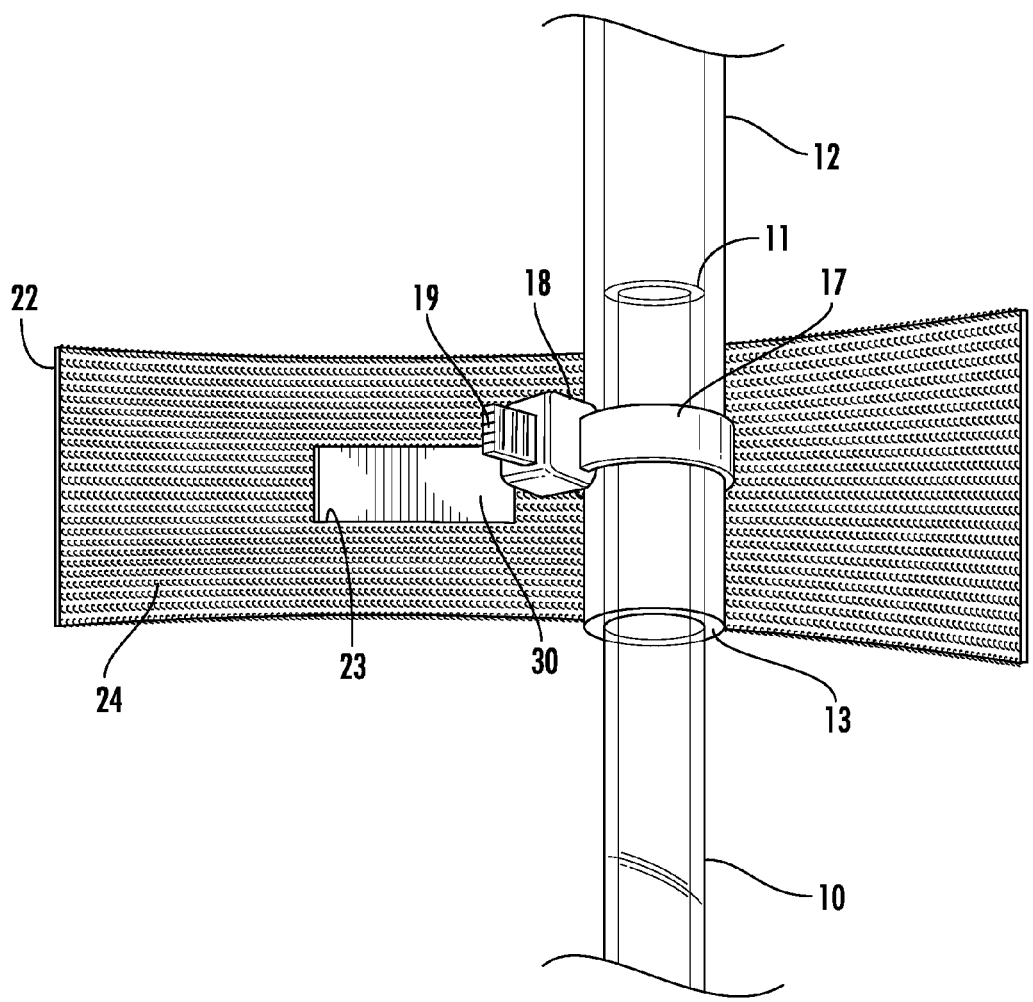
FIG. 5 is a plan view showing the cable tie and the drainage tubes positioned on the first side of the protective cover prior to wrapping the protective cover around the cable tie.
Figure 6:
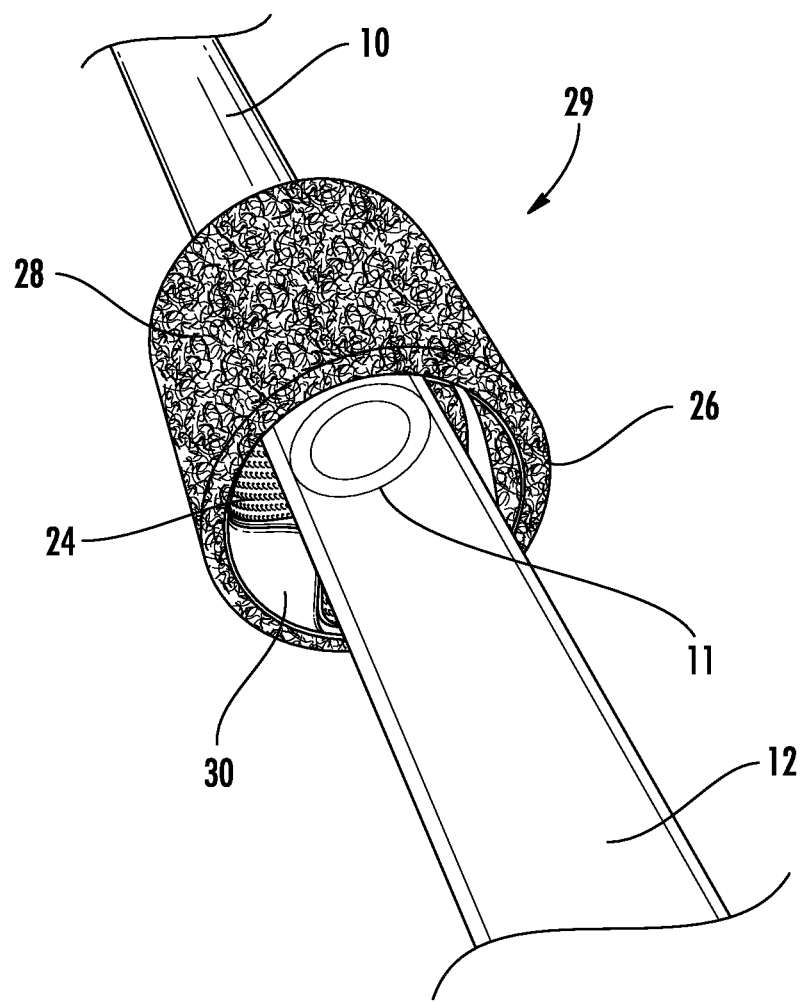
FIG. 6 is a perspective view showing the protective cover wrapped around the cable tie interconnecting the smaller diameter drainage tube with the larger diameter drainage tube.

FIG. 5 shows the location of the interconnection between the first and second drainage tubes 10, 12 with the cable tie 15 positioned on the first side 21 of the protective cover 20 having the first fastener member 22 with the VELCRO® hooks 24 and the opening 23 exposing the insert 30. The opening 23 is placed over the slotted head 18 and the sharp or jagged edge 19 of the cable tie 15 and the protective cover 20 is wrapped tightly around the drainage tubes 10, 12 and the cable tie, as illustrated by FIG. 6. Protective cover 20 has a sufficient length such that the ends overlap and the hooks 24 provided on the first fastener member 22 on the first side 21 engage with the loops 28 provided on the second fastener member 26 on the second side 29 of the protective cover. In this manner, the slotted head 18 and the sharp or jagged edge 19 of the cable tie 15 are covered by the significantly softer and less irritating loops 28 of the second fastener member 26 of the protective cover 20, as shown in FIG. 6.

It should be noted that the opening 23 could be formed through the second fastener member 26 and the slotted head 18 and the edge 19 of the cable tie 15 covered by the second fastener member. However, as a result the hooks 24 provided on the first fastener member 22 would be on the exterior second side 29 when the protective cover 20 is wrapped around the cable tie 15. The hooks 24 being rougher in texture than the loops 28 could cause some minor irritation to the skin of the patient. Furthermore, the first fastener member 22 and the second fastener member 26 may each comprise VELCRO® hooks 24 on one side and VELCRO® loops 28 on the opposite other side. In this manner, the loops 28 provided on the first fastener member 22 and the hooks 24 provided on the second fastener member 26 would engage and secure the first and second fastener members together when the fastener members are pressed together in back-to-back relationship. As in the previous embodiments, the first side 21 of the protective cover 20 would comprise the VELCRO® hooks 24 of the first fastener member 22, while the second side 29 of the protective cover 20 would comprise the VELCRO® loops 28 of the second fastener member 26.

Regardless of the foregoing detailed description of exemplary embodiments of the invention, the optimum structure of the invented device, and the manner of use, operation and steps of the invented methods, as well as reasonable equivalents thereof, are deemed to be readily apparent and understood by those skilled in the art. Accordingly, equivalent relationships to those shown in the accompanying drawing figures and described in the written description are intended to be encompassed by the present invention and its broad appended claims, the foregoing being considered as illustrative only of the general concept and principles of the invention. Furthermore, since numerous modifications and changes will readily occur to those skilled in the art, the exemplary embodiments disclosed are not intended to limit the invention to the specific configuration, construction, materials, manner of use and operation shown and described herein. Instead, all reasonably predictable and suitable equivalents and obvious modifications to the invention should be construed as falling within the scope of the invention as defined by the appended claims given their broadest reasonable construction and interpretation in view of the accompanying written description and drawing figures.

The invention claimed is:

1. A protective cover for a cable tie, comprising:
   an elongate, relatively thin first fastener member having opposed sides with a first fastener element on one of the opposed sides and a pressure sensitive adhesive on the other of the opposed sides;
   an elongate, relatively thin second fastener member having opposed sides with a second fastener element on one of the opposed sides and a pressure sensitive adhesive on the other of the opposed sides; and
   a flexible, relatively elastic insert;
   wherein the first fastener member has an opening formed therethrough configured to receive the cable tie; and
   wherein the insert is positioned over the opening on the pressure sensitive adhesive of the first fastener member; and
   wherein the pressure sensitive adhesive of the first fastener member and the pressure sensitive adhesive of the second fastener member are engaged in back-to-back relationship with the insert disposed between the first fastener member and the second fastener member.

2. The protective cover according to claim 1, wherein at least one of the first fastener member and the second fastener member comprises a length of a low-profile fastener tape.

3. The protective cover according to claim 1, wherein the first fastener element comprises VELCRO® hooks and the second fastener element comprises VELCRO® loops.

4. The protective cover according to claim 1, wherein the first fastener element comprises VELCRO® loops and the second fastener element comprises VELCRO® hooks.

5. The protective cover according to claim 1, wherein at least one of the first fastener member and the second fastener member has a length of about five (5) inches and a width of about one (1) inch.

6. The protective cover according to claim 1, wherein the opening formed in the first fastener member is generally rectangular.

7. The protective cover according to claim 6, wherein the opening is between about one-quarter (¼) inches and about three-quarters (¾) inches in width, and is between about one (1) inch and about one and one-half (1½) inches in length.

8. The protective cover according to claim 1, wherein the insert is made of a high density urethane foam.

9. The protective cover according to claim 1, wherein the insert is configured to be disposed entirely within the first fastener member and the second fastener member.

10. The protective cover according to claim 1, wherein the insert is about two (2) inches in length, about one (1) inch in width, and between about one-half (½) inch and about one (1) inch thick.

11. The protective cover according to claim 10, wherein the thickness of the insert varies in a lengthwise direction between about one-half (½) inch at one lengthwise end and about one (1) inch at the other lengthwise end.

12. A protective cover for covering a cable tie that interconnects a smaller diameter drainage tube and a larger diameter drainage tube, the protective cover comprising:
 a length of a first fastener tape having a first fastener element;
 a length of a second fastener tape having a second fastener element, the second fastener element being operable to securely engage the first fastener element; and
 an insert made of a flexible, relatively elastic material, the insert being disposed between the first fastener tape and the second fastener tape;
 wherein each of the first fastener tape and the second fastener tape has opposed sides, wherein the first fastener tape has the first fastener element on one of the opposed sides of the first fastener tape and a pressure sensitive adhesive on the other of the opposed sides of the first fastener tape, and wherein the second fastener tape has the second fastener element on one of the opposed sides of the second fastener tape and a pressure sensitive adhesive on the other of the opposed sides of the second fastener tape.

13. The protective cover according to claim 12, wherein one of the first fastener element and the second fastener element comprises VELCRO® hooks and the other of the first fastener element and the second fastener element comprises VELCRO® loops.

14. The protective cover according to claim 12, wherein at least one of the first fastener tape and the second fastener tape has an opening and the insert is positioned over the opening between the first fastener tape and the second fastener tape.

15. The protective cover according to claim 12, wherein the pressure sensitive adhesive on the other opposed side of the first fastener tape and the pressure sensitive adhesive on the other opposed side of the second fastener tape are engaged together in back-to-back relationship with the insert disposed between the first fastener tape and the second fastener tape.

16. A method for covering a cable tie that interconnects adjacent drainage tubes with a protective cover according to claim 12, the method comprising:
 using the cable tie to interconnect the adjacent drainage tubes;
 providing the protective cover;
 positioning the insert of the protective cover over an end of the cable tie; and
 wrapping one of the first fastener tape and the second fastener tape around the cable tie such that opposite ends of the protective cover overlap and the first fastener element and the second fastener element engage together to secure the protective cover over at least the end of the cable tie.

17. The method according to claim 16, wherein one of the first fastener element and the second fastener element comprises VELCRO® hooks and the other of the first fastener element and the second fastener element comprises VELCRO® loops.

18. The method according to claim 16, wherein at least one of the first fastener tape and the second fastener tape has an opening and the insert is positioned over the opening between the first fastener tape and the second fastener tape.

19. A cover for covering an end of a cable tie, comprising:
 a first side defining an outer surface having a first fastener element on the entire outer surface thereon
 a second side opposite the first side defining an outer surface and having a second fastener element on the entire outer surface thereon; and
 an insert;
 wherein an opening is formed in at least one of the first side and the second side and the opening is configured to receive the end of the cable tie;
 wherein the insert is positioned within the opening and disposed between the outer surface of the first side and the outer surface of the second side; and
 wherein when opposite ends of the cover overlap, the first fastener element on the outer surface of the first side and the second fastener element on the outer surface of the second side engage together to secure the opposite ends of the cover together with the opening and the insert positioned for covering the end of the cable tie.

20. The cover according to claim 19, wherein one of the first fastener element and the second fastener element comprises VELCRO® hooks and the other of the first fastener element and the second fastener element comprises VELCRO® loops.

* * * * *